(12) United States Patent
Carpenter (10) Patent No.: US 8,460,335 B2
(45) Date of Patent: Jun. 11, 2013

(54) METHOD OF DEFLECTING EMBOLI FROM THE CEREBRAL CIRCULATION

(75) Inventor: Judith T. Carpenter, Radnor, PA (US)

(73) Assignees: Embrella Cardiovascular, Inc., Wayne, PA (US); Edwards Lifesciences AG, Nyon (CH)

( * ) Notice: Subject to any disclaimer, the term of this patent is extended or adjusted under 35 U.S.C. 154(b) by 1654 days.

(21) Appl. No.: 11/518,865

(22) Filed: Sep. 11, 2006

(65) Prior Publication Data

US 2008/0065145 A1    Mar. 13, 2008

(51) Int. Cl.
*A61M 29/00* (2006.01)

(52) U.S. Cl.
USPC .......................................................... 606/200

(58) Field of Classification Search
USPC ................. 606/200, 113–114, 127–128, 191, 606/192, 194; 604/104, 105–109; 623/1.11, 623/1.15
See application file for complete search history.

(56) References Cited

U.S. PATENT DOCUMENTS

| | | | |
|---|---|---|---|
| 4,619,246 A | 10/1986 | Molgaard-Nielsen et al. |
| 5,634,942 A | 6/1997 | Chevillon et al. |
| 5,662,671 A | 9/1997 | Barbut et al. |
| 5,695,519 A | 12/1997 | Summers et al. |
| 5,769,816 A | 6/1998 | Barbut et al. |
| 5,911,734 A | 6/1999 | Tsugita et al. |
| 5,989,281 A | 11/1999 | Barbut et al. |
| 5,993,469 A | 11/1999 | McKenzie et al. |
| 6,027,520 A | 2/2000 | Tsugita et al. |
| 6,042,598 A | 3/2000 | Tsugita et al. |
| 6,117,154 A | 9/2000 | Barbut et al. |
| 6,152,946 A | 11/2000 | Broome et al. |
| 6,235,045 B1 | 5/2001 | Barbut et al. |
| 6,245,088 B1 * | 6/2001 | Lowery .......................... 606/200 |
| 6,251,122 B1 | 6/2001 | Tsukernik |
| 6,254,563 B1 | 7/2001 | Macoviak et al. |
| 6,258,120 B1 | 7/2001 | McKenzie et al. |
| 6,270,513 B1 | 8/2001 | Tsugita et al. |
| 6,336,934 B1 | 1/2002 | Gilson et al. |
| 6,346,116 B1 | 2/2002 | Brooks et al. |
| 6,348,063 B1 | 2/2002 | Yassour et al. |
| 6,361,545 B1 | 3/2002 | Macoviak et al. |
| 6,371,935 B1 | 4/2002 | Macoviak et al. |
| 6,371,969 B1 | 4/2002 | Tsugita et al. |
| 6,375,670 B1 | 4/2002 | Greenhalgh |
| 6,391,044 B1 | 5/2002 | Yadav et al. |

(Continued)

FOREIGN PATENT DOCUMENTS

WO    WO 2006/076505 A2    7/2006

OTHER PUBLICATIONS

U.S. Appl. No. 12/440,839, filed Mar. 11, 2009, Carpenter.
U.S. Appl. No. 12/685,539, filed Jan. 11, 2010, Carpenter et al.

(Continued)

*Primary Examiner* — Gary Jackson
*Assistant Examiner* — Lindsey Bachman
(74) *Attorney, Agent, or Firm* — David L. Hauser; Pui Tong Ho (57) ABSTRACT

Disclosed is a blood debris deflector, for preventing embolization during a surgical procedure, and methods for insertion and removal of the deflector. The method can include the steps of advancing an embolic deflection device through a first side branch vessel and into the main vessel, manipulating the deflection device such that it covers the opening to a second side branch vessel, and inverting the deflection device to remove the device from a patient.

11 Claims, 14 Drawing Sheets

U.S. PATENT DOCUMENTS

| | | | |
|---|---|---|---|
| 6,395,014 B1 * | 5/2002 | Macoviak et al. | 606/200 |
| 6,423,086 B1 | 7/2002 | Barbut et al. | |
| 6,447,530 B1 | 9/2002 | Ostrovsky et al. | |
| 6,499,487 B1 | 12/2002 | McKenzie et al. | |
| 6,511,497 B1 | 1/2003 | Braun et al. | |
| 6,537,297 B2 | 3/2003 | Tsugita et al. | |
| 6,547,760 B1 | 4/2003 | Samson et al. | |
| 6,626,937 B1 | 9/2003 | Cox | |
| 6,645,221 B1 | 11/2003 | Richter | |
| 6,673,089 B1 | 1/2004 | Yassour et al. | |
| 6,695,811 B2 | 2/2004 | Samson et al. | |
| 6,695,864 B2 | 2/2004 | Macoviak et al. | |
| 6,706,053 B1 | 3/2004 | Boylan et al. | |
| 6,726,702 B2 | 4/2004 | Khosravi | |
| 6,740,112 B2 | 5/2004 | Yodfat et al. | |
| 6,866,680 B2 | 3/2005 | Yassour et al. | |
| 6,962,598 B2 | 11/2005 | Linder et al. | |
| 6,989,019 B2 | 1/2006 | Mazzocchi et al. | |
| 6,994,092 B2 | 2/2006 | van der Burg et al. | |
| 7,083,633 B2 | 8/2006 | Morrill et al. | |
| 7,112,213 B2 | 9/2006 | Maahs | |
| 7,144,408 B2 | 12/2006 | Keegan et al. | |
| 7,172,614 B2 | 2/2007 | Boyle | |
| 7,174,636 B2 | 2/2007 | Lowe | |
| 7,217,255 B2 | 5/2007 | Boyle et al. | |
| 7,229,463 B2 | 6/2007 | Sutton et al. | |
| 7,229,464 B2 | 6/2007 | Hanson et al. | |
| 7,232,453 B2 | 6/2007 | Shimon | |
| 7,235,061 B2 | 6/2007 | Tsugita | |
| 7,241,304 B2 | 7/2007 | Boyle et al. | |
| 7,241,305 B2 | 7/2007 | Ladd | |
| 7,244,267 B2 | 7/2007 | Huter et al. | |
| 7,252,675 B2 | 8/2007 | Denison et al. | |
| 7,261,727 B2 | 8/2007 | Thielen et al. | |
| 7,303,575 B2 | 12/2007 | Ogle | |
| 7,323,001 B2 | 1/2008 | Clubb et al. | |
| 7,367,985 B2 | 5/2008 | Mazzocchi et al. | |
| 7,604,650 B2 | 10/2009 | Bergheim | |
| 7,618,446 B2 | 11/2009 | Andersen et al. | |
| 7,670,356 B2 | 3/2010 | Mazzocchi | |
| 2002/0077596 A1 * | 6/2002 | McKenzie et al. | 604/104 |
| 2002/0128679 A1 | 9/2002 | Turovskiy et al. | |
| 2002/0128680 A1 | 9/2002 | Pavlovic | |
| 2002/0138094 A1 | 9/2002 | Borillo et al. | |
| 2002/0143362 A1 | 10/2002 | Macoviak et al. | |
| 2002/0161394 A1 | 10/2002 | Macoviak et al. | |
| 2002/0169437 A1 | 11/2002 | Macoviak et al. | |
| 2002/0169474 A1 | 11/2002 | Kusleika | |
| 2003/0120304 A1 | 6/2003 | Kaganov et al. | |
| 2003/0125801 A1 | 7/2003 | Yodfat et al. | |
| 2003/0158574 A1 | 8/2003 | Esch et al. | |
| 2003/0208224 A1 | 11/2003 | Broome | |
| 2003/0220667 A1 | 11/2003 | van der Burg et al. | |
| 2004/0010307 A1 | 1/2004 | Grad et al. | |
| 2004/0010308 A1 | 1/2004 | Zafrir-Pachter | |
| 2004/0024416 A1 | 2/2004 | Yodfat et al. | |
| 2004/0034386 A1 * | 2/2004 | Fulton et al. | 606/200 |
| 2004/0088002 A1 | 5/2004 | Boyle et al. | |
| 2004/0093014 A1 | 5/2004 | Ho et al. | |
| 2004/0111111 A1 | 6/2004 | Lin | |
| 2004/0158281 A1 | 8/2004 | Boylan et al. | |
| 2004/0167568 A1 | 8/2004 | Boyle et al. | |
| 2004/0167613 A1 | 8/2004 | Yodfat et al. | |
| 2004/0215167 A1 | 10/2004 | Belson | |
| 2005/0085847 A1 | 4/2005 | Galdonik et al. | |
| 2005/0119688 A1 | 6/2005 | Bergheim | |
| 2005/0267516 A1 | 12/2005 | Soleimani et al. | |
| 2005/0283185 A1 | 12/2005 | Linder et al. | |
| 2006/0015138 A1 | 1/2006 | Gertner | |
| 2006/0015141 A1 | 1/2006 | Linder et al. | |
| 2006/0058833 A1 | 3/2006 | VanCamp et al. | |
| 2006/0129180 A1 | 6/2006 | Tsugita et al. | |
| 2006/0161241 A1 | 7/2006 | Barbut et al. | |
| 2006/0241678 A1 | 10/2006 | Johnson et al. | |
| 2006/0253148 A1 | 11/2006 | Leone et al. | |
| 2006/0287670 A1 | 12/2006 | Pal | |
| 2006/0293706 A1 | 12/2006 | Shimon | |
| 2007/0043435 A1 | 2/2007 | Seguin et al. | |
| 2007/0123931 A1 | 5/2007 | Gilson et al. | |
| 2007/0135834 A1 | 6/2007 | Clubb et al. | |
| 2007/0270901 A1 | 11/2007 | Shimon et al. | |
| 2008/0004688 A1 | 1/2008 | Spenser et al. | |
| 2008/0051807 A1 | 2/2008 | St. Goar et al. | |
| 2008/0065146 A1 | 3/2008 | Mazzocchi et al. | |
| 2008/0065147 A1 | 3/2008 | Mazzocchi et al. | |
| 2008/0109055 A1 | 5/2008 | Hlavka et al. | |
| 2008/0114440 A1 | 5/2008 | Hlavka et al. | |
| 2008/0140110 A1 | 6/2008 | Spence | |
| 2008/0140189 A1 | 6/2008 | Nguyen et al. | |
| 2008/0255603 A1 | 10/2008 | Naor et al. | |
| 2008/0275489 A1 | 11/2008 | Kinst et al. | |
| 2009/0062908 A1 | 3/2009 | Bonhoeffer et al. | |
| 2010/0312268 A1 | 12/2010 | Belson | |

OTHER PUBLICATIONS

U.S. Appl. No. 12/685,560, filed Jan. 11, 2010, Carpenter et al.
U.S. Appl. No. 12/685,570, filed Jan. 11, 2010, Carpenter et al.
U.S. Appl. No. 12/685,591, filed Jan. 11, 2010, Carpenter et al.
International Preliminary Report on Patentability, PCT/US07/78170 mailed Mar. 17, 2009, p. 5.
International Search Report dated Mar. 2, 2010 for PCT App. No. PCT/US2010/020530.
U.S. Appl. No. 12/892,767, filed Sep. 28, 2010, Belson.

* cited by examiner

METHOD OF DEFLECTING EMBOLI FROM THE CEREBRAL CIRCULATION

BACKGROUND OF THE INVENTION

Endovascular procedures are being used more and more frequently to treat various cardiac and vascular surgical problems. Blocked arteries can be treated with angioplasty, endarterectomy, and/or stenting, using minimally invasive endovascular approaches. Aneurysms can be repaired by endovascular techniques. Another use for endovascular surgery is the treatment of cardiac valvular disease. Valvuloplasties are already being done endovascularly and percutaneous valve replacement will surely follow, as it has already been tested in Europe. A major problem which is common to all these endovascular manipulations is that plaque found in the diseased vessels and valves can be dislodged and result in embolization. A major drawback to endovascular treatment of cardiac valves and arteries in the heart or thoracic aorta is that the dislodged debris can embolize into the carotid vessels resulting in catastrophic consequences such as stroke or even death. Attempts have been made to protect the cerebral vasculature with filters and other devices, but the inadequacy of the present art is obvious in the fact that these devices are rarely used. The plethora of pending patent applications for such protection devices suggests both the inadequacy of the present art and the need for improved devices.

The majority of devices described are filters. The problems with filters include difficulty in placement and retrieval as well as the possibility that a filter will fill abruptly causing blockage of the artery prior to removal of the filter. Cerebral protection requires placement of filters in the carotid arteries, which has the additional drawback of manipulation of the carotid vessels during filter placement while the cerebral vasculature is still unprotected. The risk of stroke for a carotid arteriogram done by cannulation of the carotid artery is 1% compared to an arteriogram done from injection into the aorta without selective cannulation which carries minimal risk. The risk of cannulating a carotid artery, navigating a catheter containing a filter into position, and deploying the filter would likely carry an even higher stroke risk. Patients requiring cardiac or aortic arch procedures are high risk candidates for having carotid disease. The chance of causing a stroke by the placement of the protective device into both carotid arteries makes the risk of using these devices prohibitive. The time and skill necessary to selectively cannulate both carotid arteries for filter placement has also contributed to the decision not to use them despite the stroke risk of unprotected cardiac and aortic arch procedures.

BRIEF DESCRIPTION OF THE INVENTION

The present invention comprises a deflector umbrella. In use, the invention is placed into the aortic arch by the Seldinger technique, preferably through the right arm but it may also be placed via the femoral artery. It is deployed in the aortic arch, where the umbrella is opened and pulled back into position to cover the ostia of both the brachiocephalic and left common carotid arteries.

DETAILED DESCRIPTION OF THE INVENTION

The deflector ("umbrella") of the present invention is positioned prior to any manipulation of the heart or thoracic aorta. It is simple to place and carries only the risk of catheterizing the aorta through the arm or leg, which is minimal. The umbrella is opened in the thoracic aorta and positioned to cover the ostia of both the brachiocephalic and left common carotid arteries. This position prevents clots or debris from entering the cerebral circulation through either the right or left carotid arteries with one simple device. Any debris from the cardiac or aortic procedure is deflected downstream. After the procedure is complete, the umbrella is inverted by means of a sheath extended over the catheter wire, which then wholly or partially covers the inverted umbrella prior to withdrawal. Should any clot or debris be attached to the outer side of the umbrella, it will be captured in the inverted umbrella and withdrawn. A major advantage of the device is that one size fits all, so it can be kept available in stock.

Figure 5:
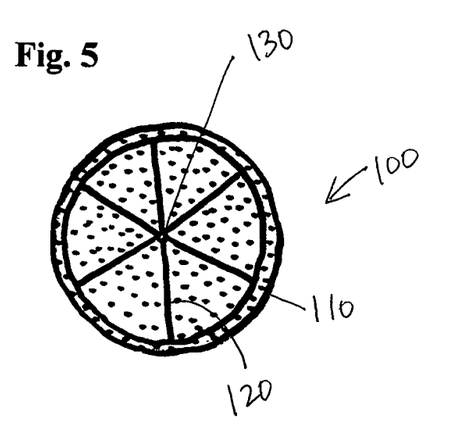
FIG. 5 depicts the deflector of the present invention.

The umbrella is preferably dome-shaped with an adequate diameter to cover the ostia of both the brachiocephalic and left common carotid arteries, made of a material with pores or similar openings or permeability to allow the flow of blood into the cerebral circulation, but able to deflect or trap particles of a size which could cause a stroke (as depicted in FIG. 5.) The edge of the umbrella is preferably a flexible, porous donut shape, similar to the edge of a vaginal diaphragm, allowing a good seal with the curved aortic wall. The edge will preferably contain a nitinol wire ring. The dome part of the umbrella preferably has struts or ribs to assist in the opening and closing of the umbrella and to help maintain its position. The center of the umbrella preferably has a knob or similar projection on the inside surface to which the struts are attached. The deflector is pushed out of the delivery catheter with a tube which engages this knob. This knob helps with the opening of the umbrella. The knob remains attached to the umbrella "handle", and the guide wire used to pull the umbrella into position. The device may also be made to open as a result of its construction material, for example, nitinol or polymer, elastically resuming its shape after being released from its sheath.

When the umbrella is to be closed, a tube or sheath of larger diameter than the knob is extended over the guide wire until it engages the knob. The umbrella is pulled back so that it inverts and is enclosed in the tube for removal. Inverting the device assures that no trapped particles escape into the bloodstream. The device is preferably constructed of polymer, fabric, metal, or a combination of these materials. The device may also optionally be equipped with radio-opaque markers or other structural parts which are radio-opaque for aid in placement guidance.

Another embodiment of the device has a rolled edge.

The device may also have a flat porous edge.

Another embodiment of the device has no struts, but instead has a nitinol skeleton.

Another embodiment has multiple wires to position and anchor the device.

Another embodiment of the device has anchors at the edges which help to maintain its position during the procedure.

Another embodiment of the device is parachute-like, with a ring gasket at its edge. The gasket would be held firmly in position over the ostia of the brachiocephalic and left common carotid arteries. The billowy porous middle section would deflect or trap clot and debris on its exterior surface while causing minimal resistance in the aorta. The middle portion would be inverted as it is removed by pulling on wires attached to its center, capturing any clot stuck to it.

Alternatively, the center of the device may comprise a screen, which fits more snugly against the aortic wall, with a very small profile, further preventing resistance to downstream aortic bloodflow. Again the device would be removed by inversion, capturing any debris stuck to it prior to removal.

The device may be round, oval or rectangular or of another shape to assist in sealing of the edge against the wall of the aorta, covering the ostia of both the brachiocephalic and left common carotid arteries and maintaining a low profile within the lumen of the aorta.

This device could be modified in size in another embodiment in order to be used to cover the ostia of different vessels.

The device may be coated with something which prevents clots (e.g., heparin).

The device may be deployed through an artery of the arm, or through the femoral artery. The preferred method would be through the right arm, if possible, as this would allow the device to be pulled back against the aortic wall to place it (FIG. 3).

When deployed through the femoral artery (FIG. 4), the opening of the umbrella would be different and the umbrella would be pushed against the aortic wall over the brachiocephalic and left common carotid openings rather than being pulled back. A wire would be cannulated into the brachiocephalic artery in this case to ensure correct positioning of the device. The device would be modified to allow this method of delivery and positioning. In this embodiment, the knob would be on the outside of the umbrella and the handle would be a firm catheter to allow pushing. In this case, retrieval of the device would involve inversion and closing of the "umbrella" by drawstring or another method.

Brachial Artery Insertion of the Device.

Figure 1:
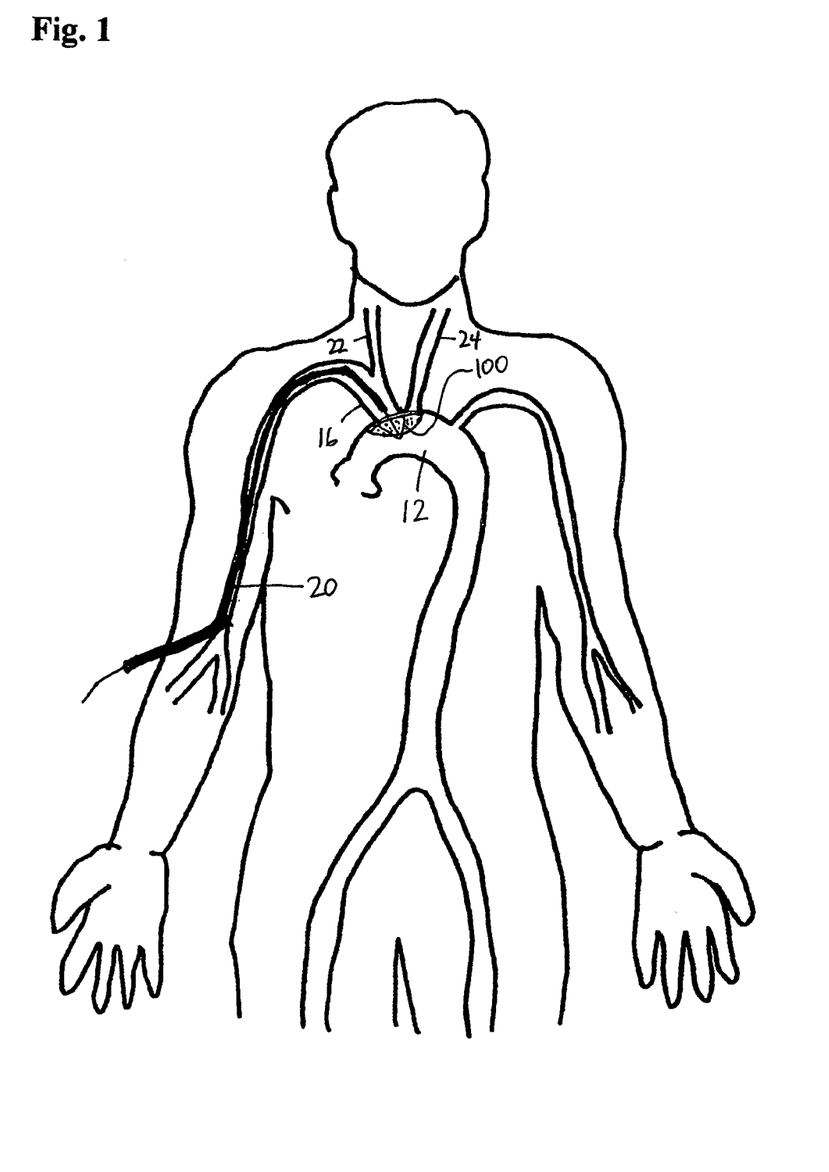
FIG. 1 depicts brachial artery insertion of the deflector of the present invention.

Referring now to FIG. 1, the deflector 100 is delivered via percutaneous insertion into the right brachial artery 20 and is guided into the aortic arch 12. There it is deployed and then pulled back into position to cover the ostia of the innominate 16 and left common carotid 24 arteries. The device 100 deflects embolic debris during aortic and cardiac procedures, allowing the flow of blood through into the cerebral circulation (carotid arteries) but not permitting the passage of particulate debris.

Femoral Artery Insertion of the Device.

Figure 2:
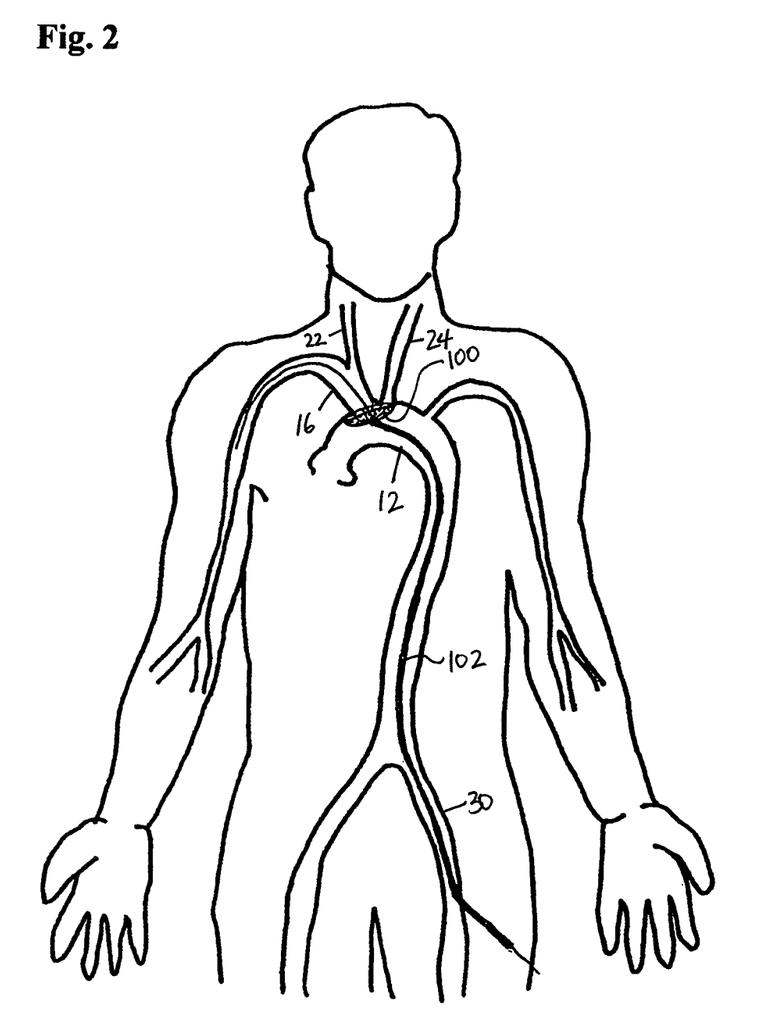
FIG. 2 depicts femoral artery insertion of the deflector of the present invention.

Referring now to FIG. 2, the deflector 100 is delivered via percutaneous insertion into the femoral artery 30 and is guided into the aortic arch 12. After catheterization of the innominate artery 16, the device 100 is passed over the wire and brought into position covering the ostia of the innominate 16 and left common carotid 24 arteries.

Deployment of the Device via Arm Approach.

Figure 3A:
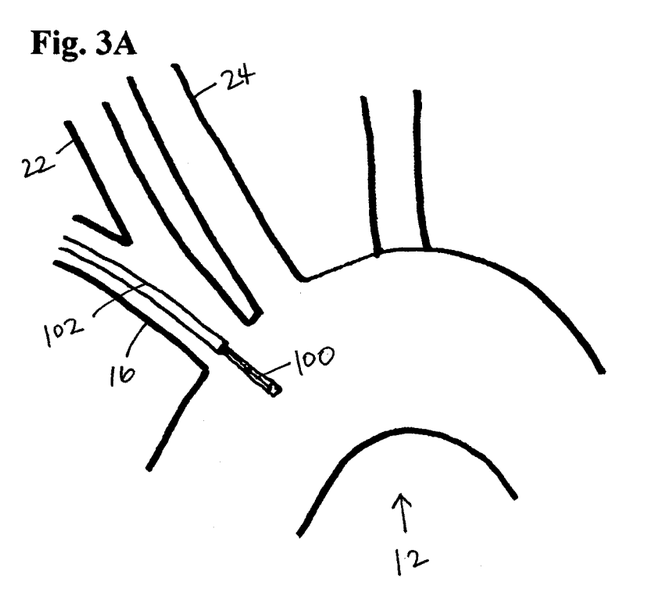
FIGS. 3A-E depict the preferred method of deployment of the deflector of the present invention through the patient's right arm, thus allowing the deflector to be pulled back against the aortic wall to place it.
Figure 3B:
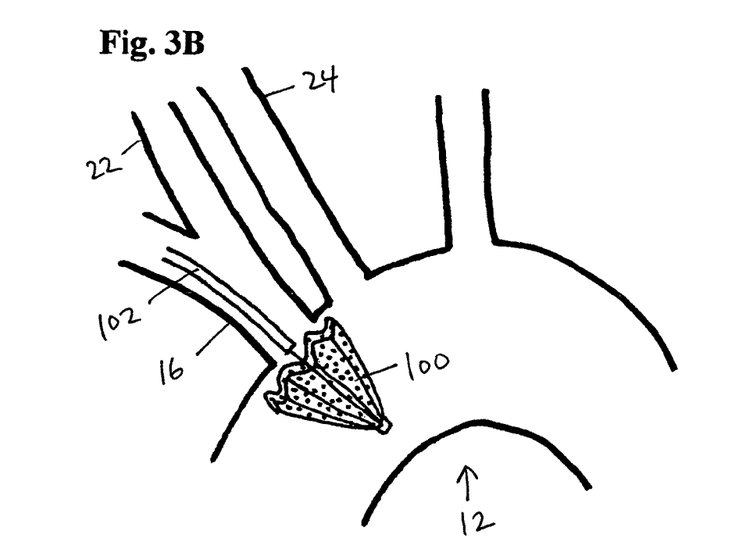
Figure 3C:
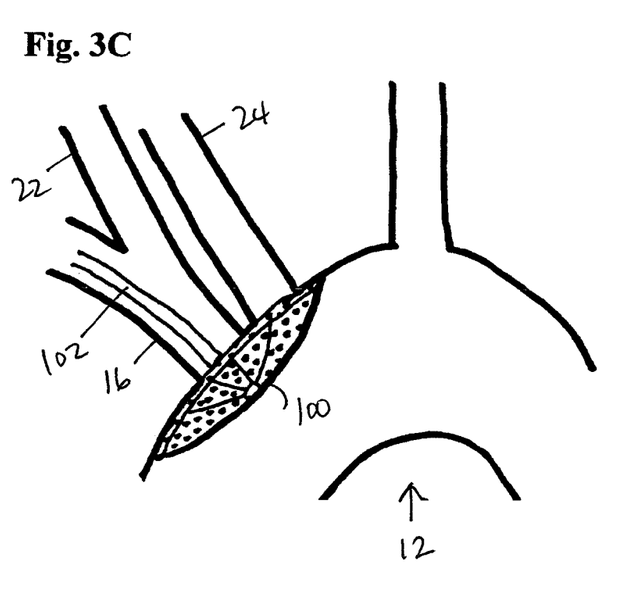
Figure 3D:
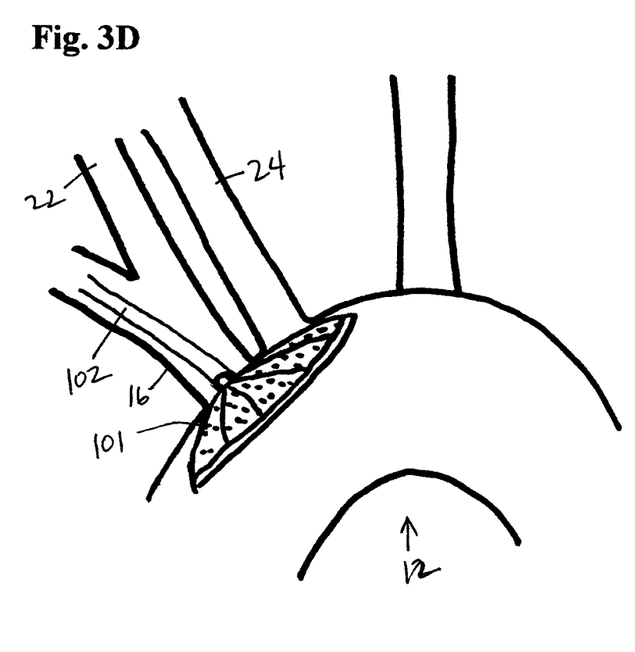
Figure 3E:
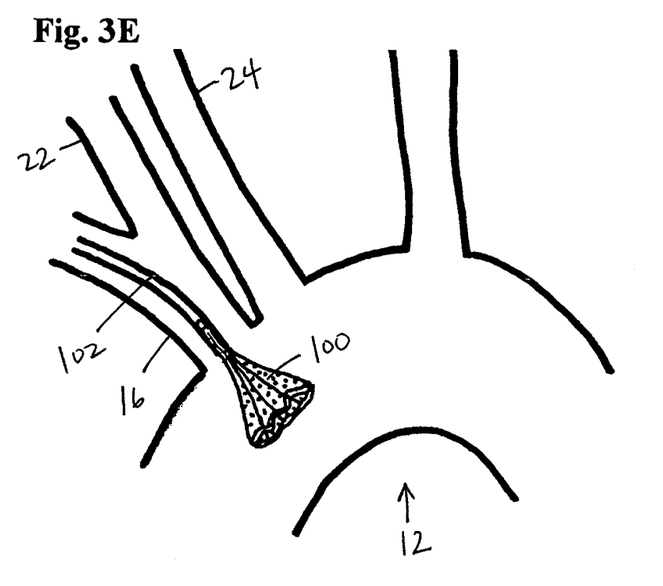

Referring now to FIGS. 3A-E, percutaneous access to the circulation via the right arm is performed and a wire guided into the aortic arch 12 after exiting the innominate artery 16. The device 100 is placed over the wire and guided into the aortic arch 12. The covering outer sheath 102 which encapsulates the device 100 is retracted (FIG. 3A), exposing the device 100 to the aortic bloodstream. The device 100 is then opened in the aortic arch 12 (FIG. 3B). The device 100 is pulled back into position, covering the ostia of the innominate 16 and left common carotid 24 artery. The device 100 allows the passage of blood through to the carotid arteries 22, 24, but deflects debris generated by aortic or cardiac surgery away from these arteries. At the completion of the debris producing concomitant procedure, the device 100 is closed by inverting the covering cap 101 (FIG. 3D). The device 100 is then withdrawn into a covering sheath 102 (FIG. 3E) to completely encapsulate it prior to removal from the arm access artery. Any trapped debris is enfolded within the closed cap 101, safely and securely within the covering sheath 102.

Deployment of the Device via Femoral Approach.

Figure 4A:
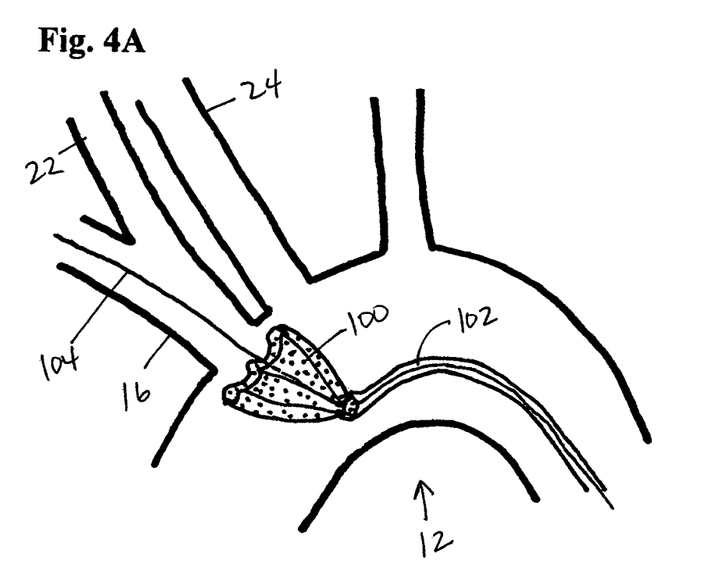
FIGS. 4A-F depict an alternative method of deployment of the deflector of the present invention through the femoral artery wherein the deflector is pushed against the aortic wall over the brachiocephalic and left common carotid openings.
Figure 4B:
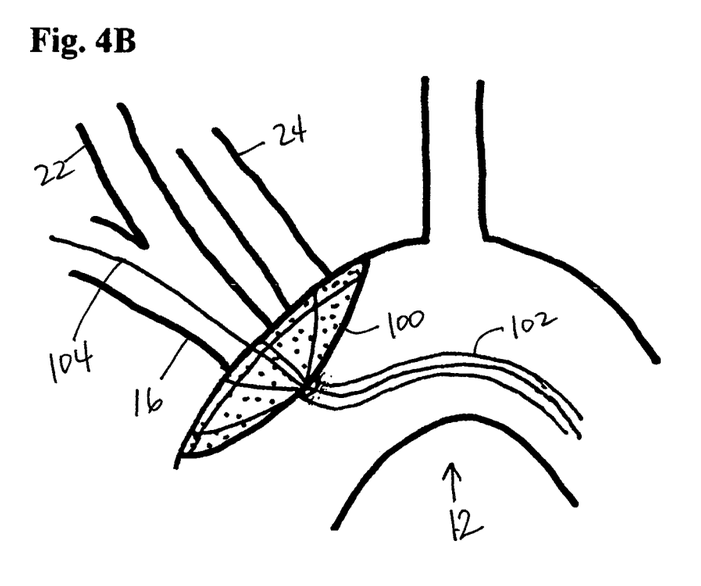
Figure 4C:
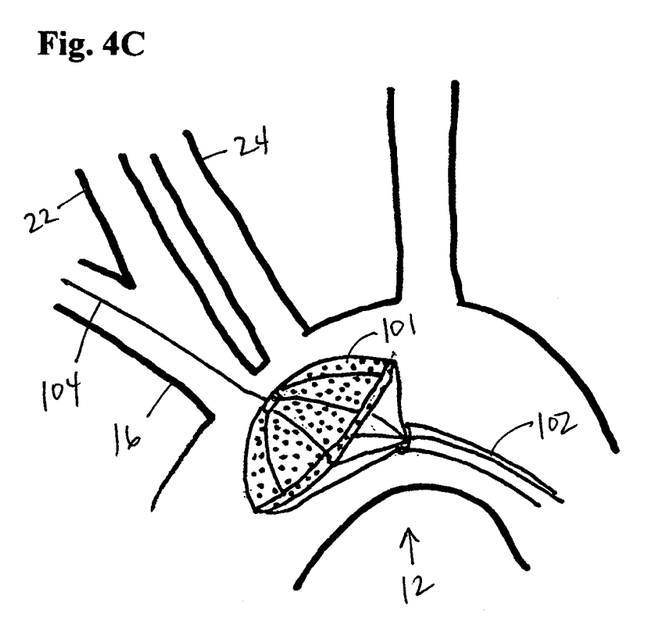
Figure 4D:
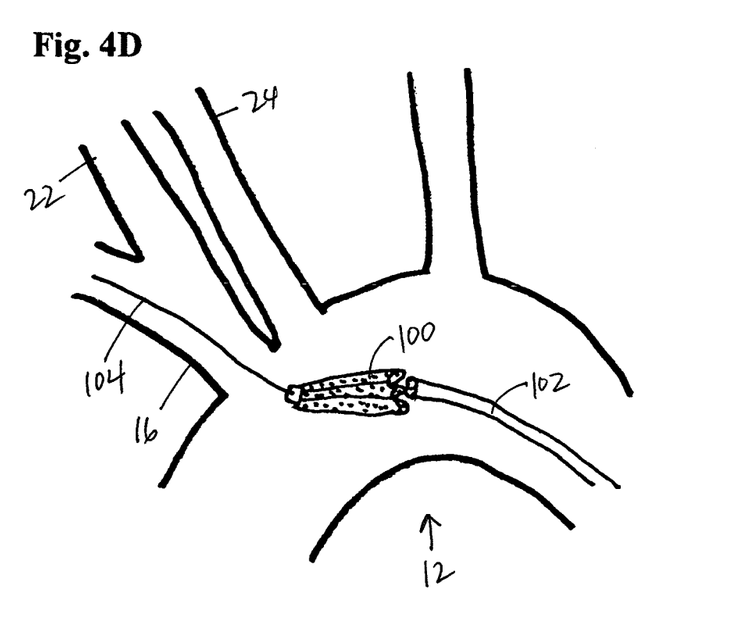
Figure 4E:
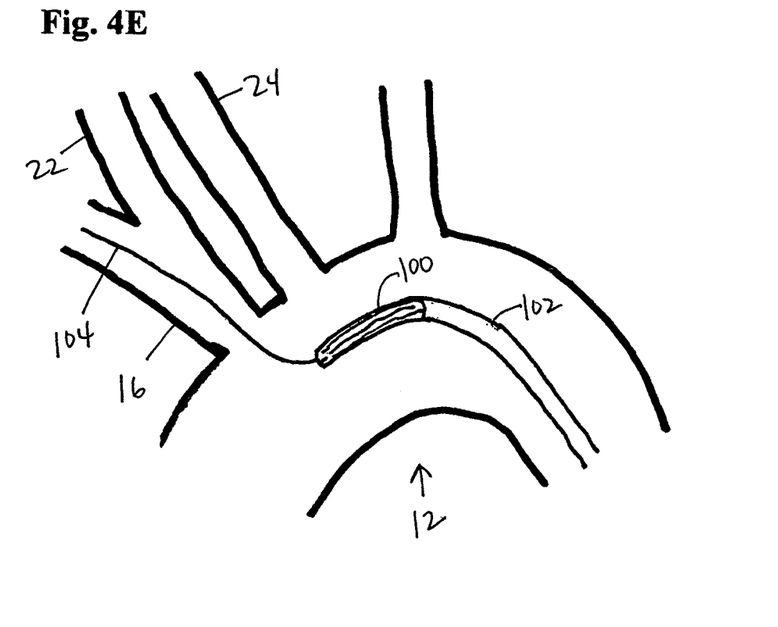
Figure 4F:
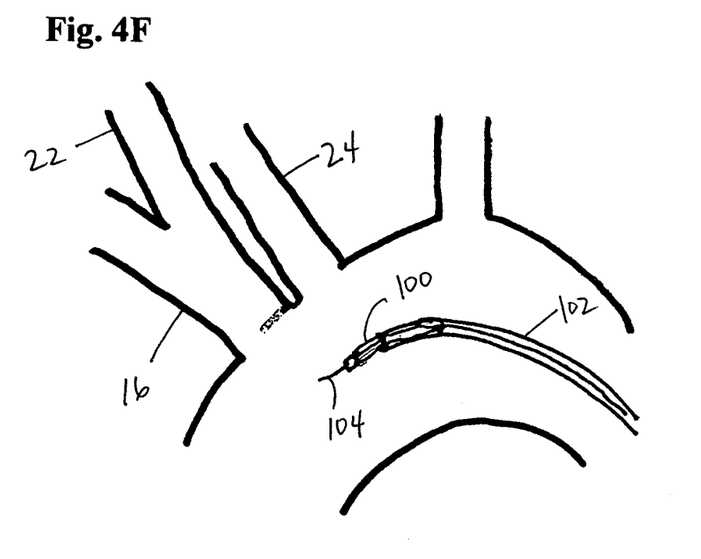

Referring now to FIGS. 4A-F, the innominate artery 16 is catheterized with a wire 104 placed via femoral access. Over the wire 104, the device 100 is guided into position in the aortic arch 12, where it is deployed by unsheathing (FIG. 4A). The device 100 is then pushed over the wire 104 into position securely covering the ostia of the innominate 16 and left common carotid 24 arteries (FIG. 4B). The device 100 allows the passage of blood through to the carotid arteries 22, 24, but deflects debris generated by aortic or cardiac surgery away from these arteries 22, 24. At the completion of the debris producing concomitant procedure, the device 100 is closed by inverting the covering cap 101 (FIG. 4C), shown here by means of drawstrings. The device 100 is then collapsed (FIG. 4D) and withdrawn into a covering sheath 102 (FIG. 4E) to completely encapsulate it prior to removal from the femoral artery 30. Any trapped debris is enfolded within the closed cap 101, safely and securely within the covering sheath 102. The wire 104 and device 100 are then withdrawn from the femoral access.

Embolic Deflecting Device.

Referring now to FIG. 5, the deflector 100 of the present invention, viewed from above, is dome-shaped with an adequate diameter to cover the ostia of both the brachiocephalic 16 and left common carotid 24 arteries, made of a material with pores to allow the flow of blood, but deflect or trap particles of a size which could cause a stroke. The edge 110 of the umbrella 100 is a flexible, porous donut, similar to the edge of a diaphragm, allowing a good seal with the curved aortic wall. The edge 110 will preferably contain a nitinol wire ring. The dome part of the umbrella 100 has struts 120 to assist in the opening and closing of the umbrella 100 and to help maintain its position.

The center of the umbrella has a knob 130 on the inside surface to which the struts 120 are attached. The device 100 is pushed out of the delivery catheter with a tube which engages this knob 130. This knob 130 helps with the opening of the umbrella. The knob 130 remains attached to the umbrella "handle", the guide wire used to pull the umbrella into position. The device 100 may also open as a result of the material it is made of, nitinol or polymer, resuming its shape after being released from its sheath.

The device is constructed of polymer, fabric, metal, or a combination of these materials. The device may be provided with radioopaque markers or metal parts which are radioopaque.

Another embodiment of the device has a rolled edge. The device could also have a flat porous edge. Another embodiment of the device has no struts, but a nitinol skeleton. Another embodiment has multiple wires to position and anchor the device. Another embodiment of the device has anchors at the edges which help to maintain its position during the procedure.

Another embodiment of the device is parachute-like, with a ring gasket at its edge. The gasket would be held firmly in position over the ostia of the brachiocephalic and left common carotid arteries. The billowy porous middle section would deflect or trap clot and debris on its exterior surface while causing minimal resistance in the aorta. The middle portion would be inverted as it is removed by pulling on wires attached to its center, capturing any clot stuck to it. Alternatively, the center of the device could be a screen, which fits more snugly against the aortic wall, with a very small profile, further preventing resistance. Again the device would be removed by inversion, capturing any clot stuck to it prior to removal.

The device may be round, oval or rectangular or of another shape to assist in sealing of the edge against the wall of the aorta, covering the ostia of both the brachiocephalic and left common carotid arteries and maintaining a low profile within the lumen of the aorta. This device could be modified in size in another embodiment in order to be used to cover the ostia of different vessels. The device may be coated with something which prevents clots (e.g. heparin).

While the invention has been described in its preferred embodiments, it is to be understood that the words which have been used are words of description rather than of limitation and that changes may be made within the purview of the appended claims without departing from the true scope and spirit of the invention in its broader aspects. Rather, various modifications may be made in the details within the scope and range of equivalents of the claims and without departing from the spirit of the invention. The inventor further requires that the scope accorded the claims be in accordance with the broadest possible construction available under the law as it exists on the date of filing hereof (and of the application from which this application obtains priority, if any) and that no narrowing of the scope of the appended claims be allowed due to subsequent changes in the law, as such a narrowing would constitute an ex post facto adjudication, and a taking without due process or just compensation.

I claim:

1. A method of deflecting emboli flowing within a main vessel from entering first and second side branch vessels, comprising the steps of:

advancing an expandable emboli deflection device through the first side branch vessel and into the main vessel, the emboli deflection device attached to a distal end of an elongate shaft; and manipulating the deflection device such that it expands to cover the ostia of each of the first and second side branch vessels, wherein manipulating the deflection device comprises applying traction to the elongate shaft to create a seal between the deflection device and the main vessel wall over the ostia of the first and second side branch vessels;

wherein the deflection device permits blood flow from the main vessel into each of the first and second side branch vessels, but deflects emboli from entering the first and second side branch vessels.

2. The method of claim 1 wherein the first branch vessel is the brachiocephalic artery and the main vessel is the aorta.

3. The method of claim 1, wherein the second side branch vessel is the left common carotid artery.

4. The method of claim 1, wherein the emboli deflection device is advanced through a sheath that removably houses the emboli deflection device.

5. The method of claim 1, wherein the method is performed in conjunction with a cardiac procedure.

6. The method of claim 5, wherein the method is performed in conjunction with a cardiac valve replacement procedure.

7. The method of claim 5, wherein the method is performed in conjunction with a valvuloplasty procedure.

8. The method of claim 1, wherein the method is performed in conjunction with an aortic repair procedure.

9. The method of claim 6, wherein traction to the elongate shaft to create a seal is maintained during the valve replacement procedure.

10. The method of claim 1, wherein the manipulating step comprises advancing at least a portion of the deflection device from an axial orientation to a lateral orientation.

11. The method of claim 1, wherein the deflection device has a configuration having a concave surface facing the ostia of each of the first and second side branch vessels after the manipulating step.

* * * * *